US012678049B2

(12) United States Patent
Tsou et al.

(10) Patent No.: US 12,678,049 B2
(45) Date of Patent: Jul. 14, 2026

(54) PHOTOSENSITIVE DEVICE

(71) Applicant: Lextar Electronics Corporation,
Hsinchu City (TW)

(72) Inventors: Pei-Fang Tsou, Hsinchu City (TW);
Yu-Jing Fang, Hsinchu City (TW);
Cheng-Ping Chang, Hsinchu City
(TW); Yen-Chih Chou, Hsinchu City
(TW); Chun-Heng Lee, Hsinchu City
(TW); Hsiao Heng Ho, Hsinchu City
(TW)

(73) Assignee: LEXTAR ELECTRONICS
CORPORATION, Hsinchu City (TW)

( * ) Notice: Subject to any disclaimer, the term of this
patent is extended or adjusted under 35
U.S.C. 154(b) by 181 days.

(21) Appl. No.: 18/535,408

(22) Filed: Dec. 11, 2023

(65) Prior Publication Data

US 2024/0188827 A1    Jun. 13, 2024

Related U.S. Application Data

(60) Provisional application No. 63/386,921, filed on Dec.
12, 2022.

(51) Int. Cl.
*A61B 5/00*          (2006.01)
*G01J 3/26*          (2006.01)
                     (Continued)

(52) U.S. Cl.
CPC .......... *A61B 5/0075* (2013.01); *A61B 5/6802*
(2013.01); *G01J 3/26* (2013.01);
(Continued)

(58) Field of Classification Search
CPC ................ A61B 5/0075; A61B 5/6802; A61B
2562/0233; A61B 2562/185; G01J 3/26;
(Continued)

(56) References Cited

U.S. PATENT DOCUMENTS 7,196,314 B2    3/2007  Rhodes
10,854,659 B2 * 12/2020  Lee ..................... H10F 39/8057
(Continued)

FOREIGN PATENT DOCUMENTS

TW          200616218 A    5/2006
TW          202147598 A    12/2021

OTHER PUBLICATIONS

Hou, GuoJiao, Ivan Garcia, and Ignacio Rey-Stolle. "High-low
refractive index stacks for broadband antireflection coatings for
multijunction solar cells." Solar Energy 217 (2021): 29-39. (Year:
2021).*

*Primary Examiner* — Dominic J Bologna
(74) *Attorney, Agent, or Firm* — McClure, Qualey &
Rodack, LLP

(57)                    ABSTRACT
A photosensitive device is provided. The photosensitive
device includes a sensing stack, an anti-reflective layer, an
optical filter, a first electrode, and a second electrode. The
sensing stack includes a first semiconductor layer, an intrin-
sic semiconductor layer disposed on the first semiconductor
layer, and a second semiconductor layer disposed on the
intrinsic semiconductor layer. The anti-reflective layer is
disposed on a side of the sensing stack. The optical filter is
disposed on the anti-reflective layer and blocks input light
with an incident angle greater than 50 degrees. The first
electrode and the second electrode are disposed on the
sensing stack.

19 Claims, 13 Drawing Sheets

(51) Int. Cl.

| | |
|---|---|
| *G02B 5/22* | (2006.01) |
| *G02B 5/28* | (2006.01) |
| *H10F 30/223* | (2025.01) |
| *H10F 55/20* | (2025.01) |
| *H10F 77/20* | (2025.01) |
| *H10F 77/30* | (2025.01) |
| *H10F 77/40* | (2025.01) |

(52) U.S. Cl.
CPC .............. *G02B 5/22* (2013.01); *G02B 5/285* (2013.01); *H10F 30/223* (2025.01); *H10F 55/26* (2025.01); *H10F 77/206* (2025.01); *H10F 77/331* (2025.01); *H10F 77/337* (2025.01); *H10F 77/413* (2025.01); *A61B 2562/0233* (2013.01); *A61B 2562/185* (2013.01)

(58) Field of Classification Search
CPC ......... G02B 5/22; G02B 5/285; H10F 30/223; H10F 55/26; H10F 77/206; H10F 77/331; H10F 77/337; H10F 77/413
See application file for complete search history.

(56) References Cited

U.S. PATENT DOCUMENTS

| | | | |
|---|---|---|---|
| 2006/0097134 A1* | 5/2006 | Rhodes ................. | H10F 39/805 |
| | | | 250/214.1 |
| 2012/0032193 A1* | 2/2012 | Kurokawa .......... | H10F 39/8057 |
| | | | 257/443 |
| 2015/0036133 A1* | 2/2015 | Uematsu ............... | G01B 11/26 |
| | | | 250/226 |
| 2016/0123808 A1* | 5/2016 | Obermueller ............ | G01J 3/26 |
| | | | 356/326 |
| 2020/0203406 A1* | 6/2020 | Lee ........................ | H10F 39/199 |
| 2022/0115420 A1* | 4/2022 | Yoon ..................... | G01J 3/2803 |
| 2022/0131018 A1* | 4/2022 | Jeon ..................... | H10K 59/65 |
| 2022/0149212 A1* | 5/2022 | Tsou ..................... | G02B 5/208 |

* cited by examiner

1a

PHOTOSENSITIVE DEVICE

CROSS REFERENCE TO RELATED APPLICATIONS

This application claims the benefit of U.S. Provisional Application No. 63/386,921, filed 12, December 2022, and the entirety of which is incorporated by reference herein.

BACKGROUND

Technical Field

The present disclosure relates to a photosensitive device to measure users' physiological data, and use coating technology to achieve a reduction in the light-receiving angle and enhance physiological signals.

Description of the Related Art

The demand for using wearable electronic products to measure users' physiological data is gradually increasing. Specifically, these wearable electronic products obtain signals related to physiological data by measuring light reflected from the user's body (e.g., wrist). However, due to the complexity of human tissue, not all light reflected by the user's body may form useful signals.

SUMMARY

An embodiment of the present disclosure provides a photosensitive device. The photosensitive device includes a sensing stack, an anti-reflective layer, an optical filter, a first electrode, and a second electrode. The sensing stack includes a first semiconductor layer, an intrinsic semiconductor layer disposed on the first semiconductor layer, and a second semiconductor layer disposed on the intrinsic semiconductor layer. The anti-reflective layer is disposed on a side of the sensing stack. The optical filter is disposed on the anti-reflective layer and blocks input light with an incident angle of greater than 50 degrees. The first electrode and the second electrode are disposed on the sensing stack.

The photosensitive device of the present disclosure can be applied to various types of electronic devices. In order to make the features and advantages of the present disclosure more comprehensible, various embodiments are specially cited below, together with the accompanying drawings, to be described in detail as follows.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments or examples for implementing the provided photosensitive device (PD). Specific examples of features and their configurations are described below to simplify the embodiments of the disclosure, but certainly not to limit the disclosure.

The terms "about", "substantially", or the like used herein generally means within 10%, within 5%, within 3%, within 2%, within 1%, or within 0.5% of a given value or a given range. The value given herein is an approximate value, that is, the meanings of "about" or "substantially" may still be implied without the specific descriptions of "about" or "substantially".

Figure 1:
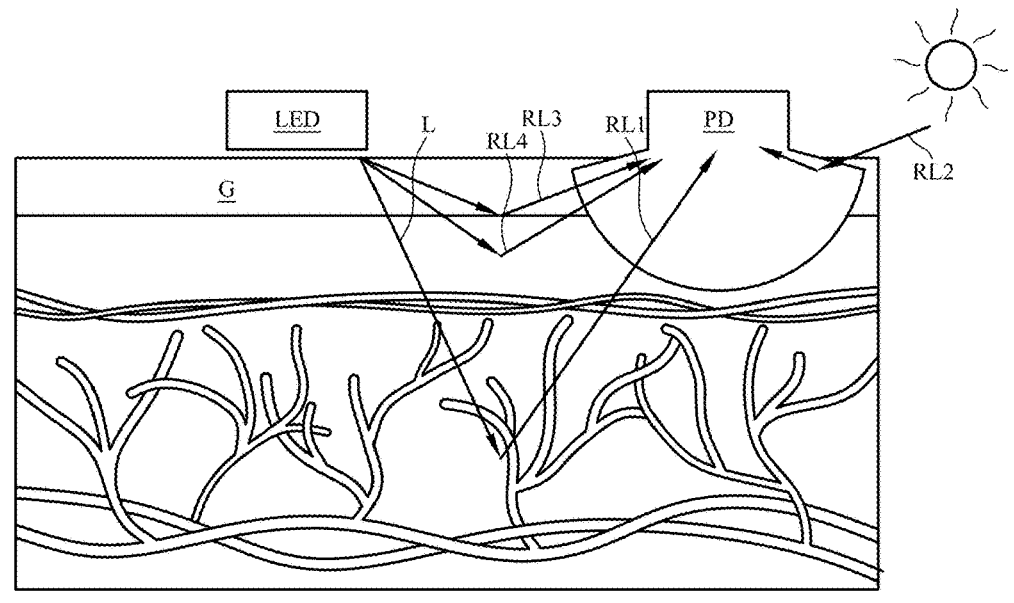
FIG. 1 is a schematic diagram showing the wearable electronic product with the light-emitting device and the photosensitive device according to some embodiments of the existing technology.

FIG. 1 is a schematic diagram showing the wearable electronic product with the light-emitting device (LED) and the photosensitive device (PD) according to some embodiments of the existing technology. As shown in the figure, the wearable electronic product emits a light L with specific wavelength through a light-emitting device thereof. Then, the light L penetrates the user's skin and interacts (e.g., reflects) with the user's body (especially the blood at deep skin). Subsequently, the wearable electronic product receives the reflected light RL1 through a photosensitive device (also called a photodetector) thereof. As a result, the wearable electronic product can determine the user's physiological characteristics based on a signal corresponding to the reflected light RL1, such as heart rate, blood oxygen, blood sugar, water content, and blood pressure.

However, the reflected lights received by the photosensitive device may not all be reflected from the user's blood at deep skin, which may further include the reflected light RL2 of the surrounding environment (e.g., from the sun), internally reflected light RL3 of the wearable electronic product itself (e.g., from a glass plate G of the wearable electronic product), reflected light RL4 of the user's tissue at superficial skin, and other possible reflected light. In other words, the signals used to represent the user's physiological characteristics that are generated from the reflected lights include effective signals that can be used to represent the user's physiological characteristics and ineffective signals that cannot be used to represent the user's physiological characteristics.

Among these signals, only the signal generated by the reflected light RL1 from the user's blood at deep skin is effective, and this signal is an alternating signal (AC) corresponding to the cardiac systolic and diastolic. The other signals generated by the reflected light RL2 from the surrounding environment, the reflected light RL3 from the wearable electronic product itself, and the reflected light RL4 from the user's skin tissue at superficial skin, etc. are ineffective, and these signals are direct signals (DC).

Figure 2:
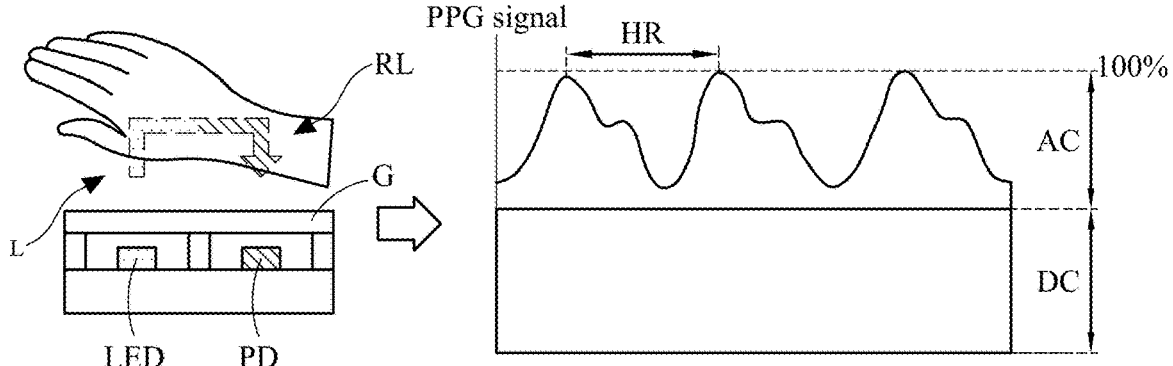
FIG. 2 is a schematic diagram showing the photoplethysmography (PPG) signal according to some embodiments of the existing technology.

FIG. 2 is a schematic diagram showing the photoplethysmography (PPG) signal according to some embodiments of the existing technology. As shown in FIG. 2, the heart rate (HR) may be presented by the distance between two adjacent hills of the PPG signal, and the heart rate is related to the AC value. Therefore, the perfusion index (PI) is defined as AC divided by DC, wherein the value of PI is positively related to the quality of the photoplethysmography signal that is used to present the user's physiological characteristics. In other words, when the proportion of the AC signal is higher (that is, the higher the PI value), the accuracy of the heart rate is higher. In some cases, the quality of the photoplethysmography signal may also be represented by signal-noise ratio (SNR). In the embodiment of FIG. 2, the AC signal only accounts for a small part (e.g., 40%) of the total measured range of the total range of the photosensitive device, while the DC signal accounts for more than half of the total measured range. That means the quality of the photoplethysmography signal is too low, and the effect of signal processing in the back end is limited.

In order to solve at least the above-mentioned problems, the present disclosure provides a photosensitive device with a collimation structure (i.e., optical film), which can effectively block light having an incident angle that is greater than a specific angle (e.g., 50 degrees), thereby effectively selecting the reflected light (e.g., the reflected light RL1) that can represent the user's physiological characteristics.

Figure 3A:
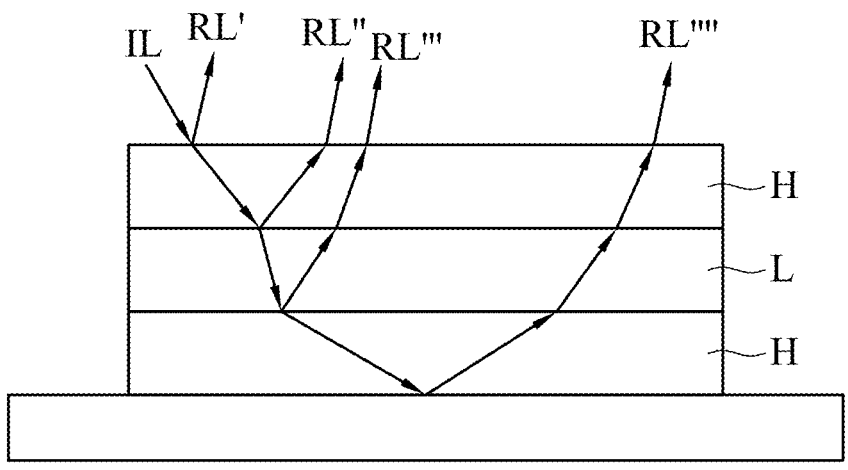
FIGS. 3A and 3B are schematic diagrams showing the principle of the collimation structure.
Figure 3B:
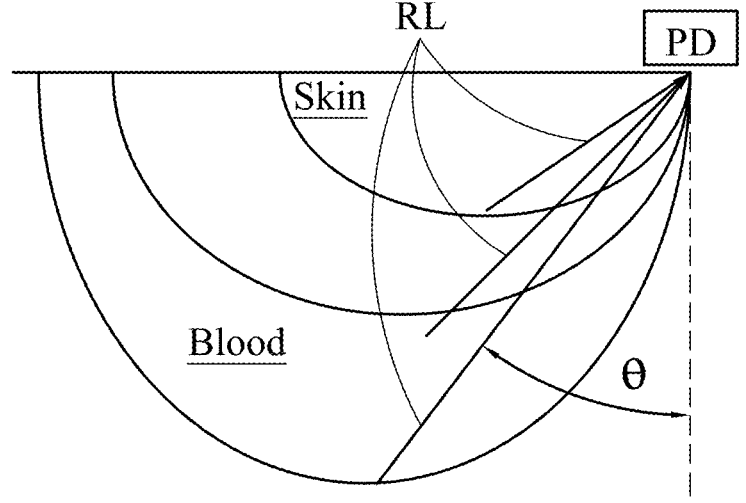

FIGS. 3A and 3B are schematic diagrams showing the principle of the collimation structure (i.e., optical film). As shown in FIG. 3A, through the arrangement of the high refractive films H and the low refractive films L that are alternately stacked, the incident light IL may interact with the interfaces of any two adjacent films to form the reflect lights RL' to RL"". As shown in FIG. 3B, each reflect light (i.e., the reflect lights RL' to RL"") has a specific incident angle θ for the photosensitive device. Therefore, the function of selecting the reflected light may be achieved by adjusting the arrangement of the high-refractive film and the low-refractive film to shield some reflected light having the specific incident angle θ. The specific instructions will be explained in detail hereinafter.

Figure 4:
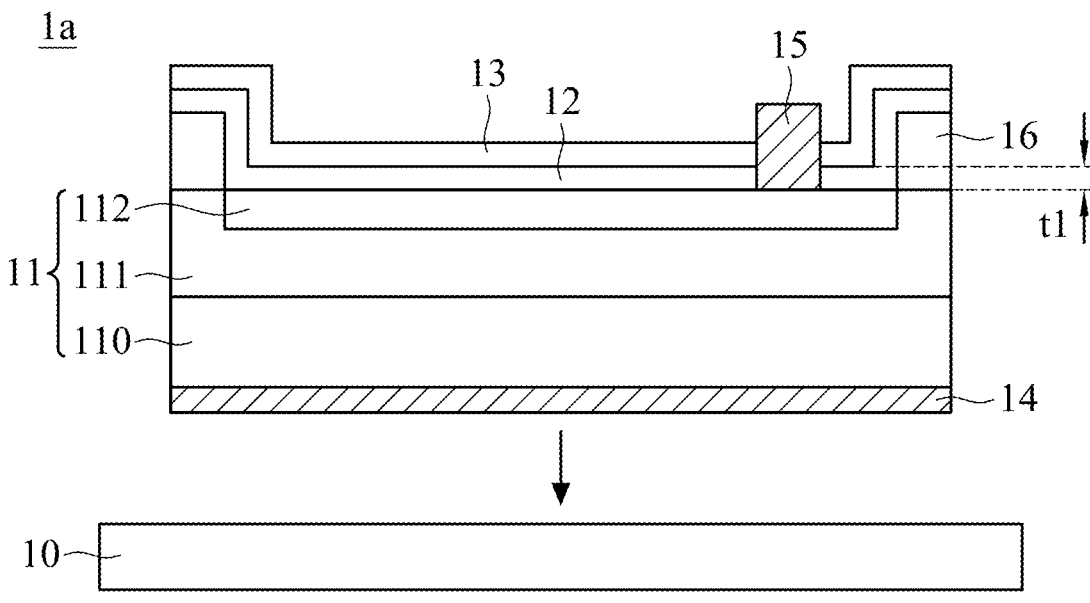
FIG. 4 is a schematic diagram showing the photosensitive device according to some embodiments of the present disclosure.

FIG. 4 is a schematic diagram showing the photosensitive device according to some embodiments of the present disclosure. As shown in FIG. 4, the photosensitive device 1a includes the sensing stack 11, the anti-reflective layer 12, the optical filter 13, the first electrode 14, and the second electrode 15. In some embodiments, the photosensitive device 1a further includes the substrate 10 that is used to carry the components or features located thereon. In some embodiments, the substrate 10 may be a printed circuit board (PCB), thin film transistor glass (TFT glass), complementary metal oxide semiconductor (CMOS) substrate, or other suitable substrates, but the present disclosure is not limited thereto. In some embodiments, the material of the substrate 10 may be or may include glass, polymer, other suitable substrates, or combinations thereof, but the present disclosure is not limited thereto. For example, the substrate 10 may be a glass substrate.

As shown in FIG. 4, the sensing stack 11 is disposed on the substrate 10. More specifically, the sensing stack 11 is configured to receive the reflected light (hereinafter, it is also called "input light") to generate a corresponding signal that refers to the user's physiological characteristics. In some embodiments, the sensing stack 11 is also called a photosensitive element that exhibits physical changes according to receiving light (e.g., produces an electric current). In some embodiments, the input light is in one of the following ranges: 495 nm to 570 nm, 600 nm to 750 nm, 760 nm to 1000 nm, 1050 nm to 1200 nm, 1250 nm to 1450 nm, and 1500 nm to 1700 nm, but the present disclosure is not limited thereto. In other words, the input light used to present the user's physiological characteristics may be green light, red light, infrared red (IR) light, or a combination thereof.

As shown in FIG. 4, the sensing stack 11 includes the first semiconductor layer 110, an intrinsic semiconductor layer 111 disposed on the first semiconductor layer 110, and the second semiconductor layer 112 disposed on the intrinsic semiconductor layer 111. In some embodiments, the first semiconductor layer 110 and the second semiconductor layer 112 may be an n-type semiconductor layer and a p-type semiconductor layer, respectively. Alternatively, the first semiconductor layer 110 and the second semiconductor layer 112 may be a p-type semiconductor layer and an n-type semiconductor layer, respectively.

In some embodiments, the n-type semiconductor layer may include: group II-VI materials, such as zinc selenide (ZnSe); or group III-V materials, such as gallium nitride (GaN), aluminum nitride (AlN), indium nitride (InN), indium gallium nitride (InGaN), aluminum gallium nitride (AlGaN), or aluminum indium gallium nitride (AlInGaN), but the present disclosure is not limited thereto. In some embodiments, the n-type semiconductor layer may contain dopants such as silicon (Si) or germanium (Ge), but the present disclosure is not limited thereto. In addition, the n-type semiconductor layer may have a single-layer or multi-layer structure.

In some embodiments, the p-type semiconductor layer may include group II-VI materials, such as zinc selenide (ZnSe); or group III-V materials, such as gallium nitride (GaN), aluminum nitride (AlN), indium nitride (InN), indium gallium nitride (InGaN), aluminum gallium nitride (AlGaN), or aluminum indium gallium nitride (AlInGaN), but the present disclosure is not limited thereto. In some embodiments, the p-type semiconductor layer may contain magnesium (Mg), carbon (C) and other dopants, but the present disclosure is not limited thereto. In addition, the p-type semiconductor layer may have a single-layer or multi-layer structure.

In some embodiments, the intrinsic semiconductor layer 111 may include at least one undoped semiconductor layer or at least one low-doped layer. For example, the intrinsic semiconductor layer 111 may be a quantum well (QW) layer, which may include indium gallium nitride ($InxGa_{1-x}N$), gallium nitride (GaN), aluminum gallium nitride (AlGaN), or aluminum indium gallium nitride (AlInGaN), but the present disclosure is not limited thereto. Alternatively, the intrinsic semiconductor layer 111 may also be a multiple quantum well (MQW) layer.

As shown in FIG. 4, the anti-reflection layer 12 is disposed on a side of the sensing stack 11 and configured to reduce reflection of the input light from the surface of the sensing stack 11, so as to increase the light receiving the amount of the sensing stack 11. In some embodiments, the anti-reflection layer 12 may include semiconductor materials, organic insulating materials, or inorganic insulating materials, but the present disclosure is not limited thereto. In some embodiments, the semiconductor material may include amorphous silicon, but the disclosure is not limited thereto. In some embodiments, the organic insulating material may include acrylic polymer, polyimide, polyester, epoxy resin, combinations thereof, or other suitable organic insulating materials. In some embodiments, inorganic insulating materials suitable for the anti-reflective layer 12 may include silicon oxide, silicon nitride, silicon oxynitride, aluminum oxide, combinations thereof, or other suitable inorganic insulating materials. For example, the material of the anti-reflective layer 11 includes silicon nitride.

In some embodiments, the thickness t1 of the anti-reflective layer 12 is from 50 nm to 100 nm. For example, the thickness t1 of the anti-reflective layer 12 may be 50 nm, 55 nm, 60 nm, 65 nm, 70 nm, 75 nm, 80 nm, 85 nm, 90 nm, 95 nm, 100 nm, or any value or range between any two of the above-mentioned values, but the present disclosure is not limited thereto. In some embodiments, the thickness t1 of the anti-reflective layer 12 may correspond to ¼λ, ¾λ, 5/4λ, 7/4λ, etc. of the wavelength of the input light to be received.

As shown in FIG. 4, the optical filter 13 is disposed on the anti-reflective layer 12 and configured to block input light with an incident angle of greater than 50 degrees. In the present disclosure, the phrase "block input light with an incident angle of greater than 50 degrees" refers to making the transmittance of the optical filter for input light with an incident angle of greater than 50 degrees lower than 50%. For example, the transmittance of the optical filter 13 for input light with an incident angle of greater than 50 degrees may be 50%, 45%, 40%, 35%, 30%, 25%, 20%, 15%, 10%, 5%, 1%, 0.1%, or any value or range between any two of the above-mentioned values, but the present disclosure is not limited thereto.

Figure 5:
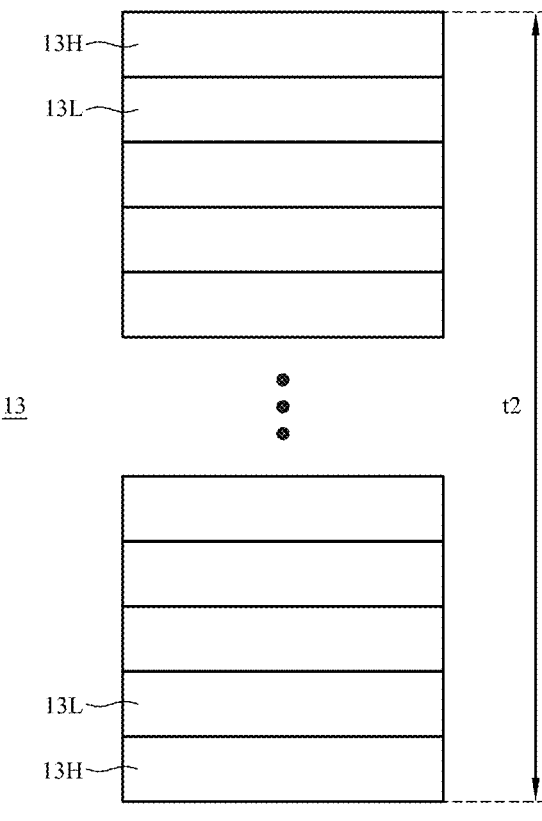
FIG. 5 is a schematic diagram showing an optical filter according to some embodiments of the present disclosure.
Figure 6:
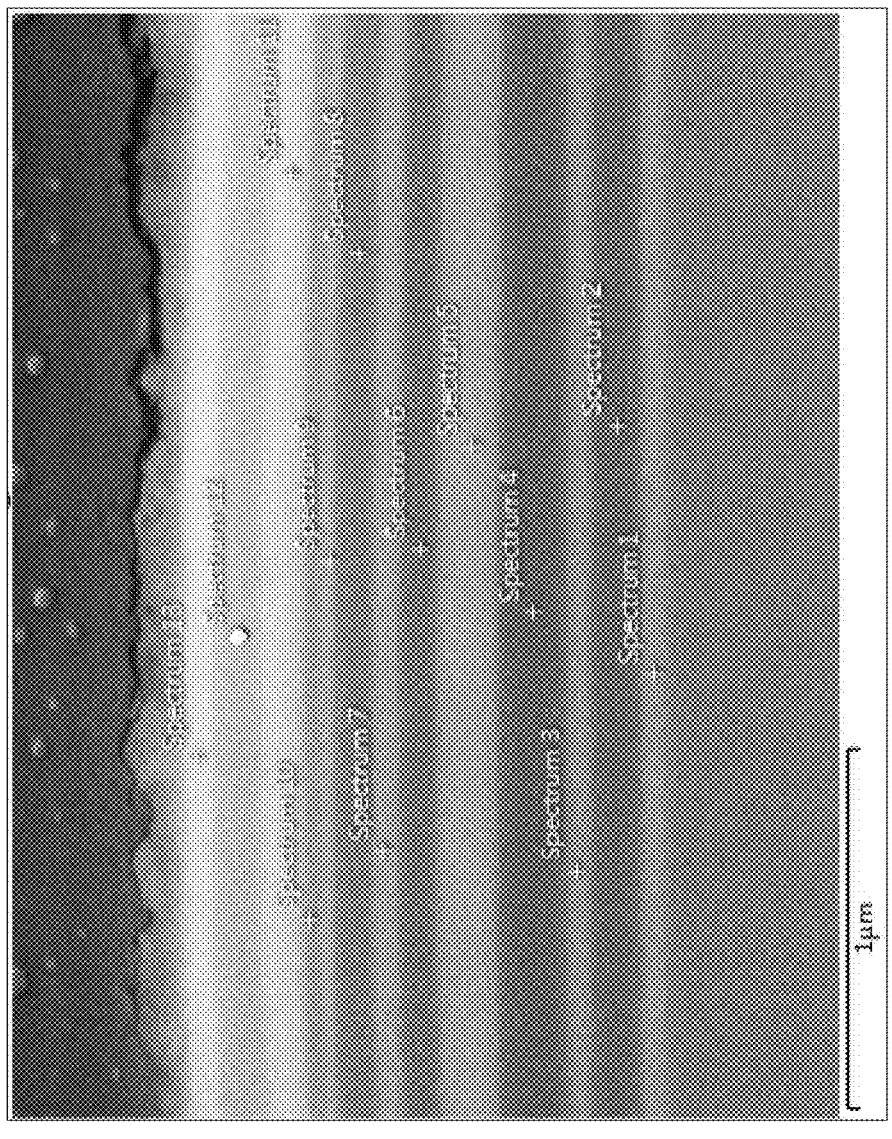
FIG. 6 is a cross-sectional view of the optical filter obtained by the scanning electron microscope (SEM) according to some embodiments of the present disclosure.

FIG. 5 is a schematic diagram showing an optical filter according to some embodiments of the present disclosure. As shown in FIG. 5, in some embodiments, the optical filter 13 includes high refractive films 13H and low refractive films 13L alternately stacked, and the total number of the high refractive films 13H and the low refractive films 13L is thirteen or more than thirteen. For example, the total number of the high refractive films 13H and the low refractive films 13L may be 13 as shown in FIG. 6 (i.e., the spectrums 1 to 13 in the figure), wherein FIG. 6 is a cross-section view of the optical filter obtained by the scanning electron microscope (SEM) according to some embodiments of the present disclosure. However, the present disclosure is not limited thereto. In other embodiments, the total number of the high refractive films 13H and the low refractive films 13L may be 14, 15, or more than 15, but the present disclosure is not limited thereto.

In some embodiments, the refractive index of the high refractive films 13H and low refractive films 13L is from 1.3 to 2.5, but the present disclosure is not limited thereto. More specifically, the refractive index of the high refractive films 13H is from 2.0 to 2.5 and the refractive index of the low refractive films 13L is from 1.3 to 1.5. For example, the refractive index of the high refractive films 13H may be 2.0, 2.1, 2.2, 2.3, 2.4, 2.5, or any value or range of any two of the above-mentioned values. For example, the refractive index of the low refractive films 13L may be 1.3, 1.35, 1.4, 1.45, 1.5, or any value or range of any two of the above-mentioned values.

As shown in FIG. 5, in some embodiments, the thickness t2 of the optical filter 13 is from 1500 nm to 1950 nm, but the present disclosure is not limited thereto. For example, the thickness t2 of the optical filter 13 may be 1500 nm, 1550 nm, 1600 nm, 1650 nm, 1700 nm, 1750 nm, 1800 nm, 1850 nm, 1900 nm, 1950 nm, or any value or range of any two of the above-mentioned values. In some embodiments, the thicknesses of any two of the high refractive films 13H are different. In some embodiments, the thicknesses of any two the low refractive films 13L are different. In some embodiments, the thicknesses of the high refractive films 13H are different from the thicknesses of the low refractive films 13L.

In some embodiments, the optical filter 13 includes a metal element, wherein the metal element may be or may include sodium, niobium, titanium, silver, barium, or a combination thereof. In some embodiments, the content of the metal element is from 15 wt % to 40 wt % based on the total weight of the optical filter 13, but the present disclosure is not limited thereto. For example, the content of the metal element may be 15 wt %, 20 wt %, 25 wt %, 30 wt %, 35 wt %, 40 wt %, or any value or range of any two of the above-mentioned values, based on the total weight of the optical filter 13. In some embodiments, the optical filter 13 may further include carbon, oxygen, silicon, or combinations thereof.

The first type of optical filter 13 of the present disclosure is shown as an example. It should be noted that the following recipes are only used to make the present disclosure clearer and easier to understand and are not intended to limit this disclosure. In the first type of optical filter 13, based on the total weight of the optical filter 13, the content of sodium is from 0 wt % to 1.13 wt %, the content of niobium is from 0 wt % to 29.51 wt %, the content of carbon is from 21.52 wt % to 39.68 wt %, the content of oxygen is from 3.79 wt % to 38.48 wt %, and the content of silicon is from 6.33 wt % to 63.85 wt %. Based on the above-mentioned composition, various recipes of the first type of optical filter 13 are shown in Table 1. Among them, any recipe shown in Table 1 may be used as a layer in the high refractive films 13H or the low refractive films 13L of the optical filter 13. For example, in the case of the optical filter 13 with thirteen layers, any of the recipes may be used as one of the thirteen layers.

TABLE 1

|  | Recipe 1 | Recipe 2 | Recipe 3 | Recipe 4 | Recipe 5 | Recipe 6 | Recipe 7 |
|---|---|---|---|---|---|---|---|
| C | 39.68 | 29.63 | 21.52 | 22.45 | 26.42 | 31.10 | 32.36 |
| O | 31.38 | 38.48 | 34.90 | 31.38 | 26.02 | 22.64 | 3.79 |
| Na | 1.13 | 1.11 | 0.67 | 0.45 | 0 | 0 | 0 |
| Si | 6.33 | 16.31 | 20.20 | 16.21 | 28.84 | 28.18 | 63.85 |
| Nb | 21.47 | 14.47 | 22.70 | 29.51 | 18.72 | 18.08 | 0 |
| Total | 100% | 100% | 100% | 100% | 100% | 100% | 100% |

Alternatively, the second type of optical filter 13 of the present disclosure is shown as an example. In the second type of optical filter 13, based on the total weight of the optical filter 13, the content of titanium is from 16.40 wt % to 36.36 wt %, the content of silver is from 0 wt % to 2.38 wt %, the content of carbon is from 1.54 wt % to 27.47 wt %, the content of oxygen is between 31.46 wt % and 47.01 wt %, and the content of silicon is from 12.92 wt % to 42.99 wt %, and the average and the standard deviation of the compositions of the second type of optical filter 13 are shown in Table 2.

TABLE 2

|  | Max | Min | Average | Standard Deviation |
|---|---|---|---|---|
| C | 27.47 | 1.54 | 6.69 | 7.37 |
| O | 47.01 | 31.46 | 42.77 | 4.63 |
| Si | 42.99 | 12.92 | 24.75 | 9.72 |
| Ti | 36.36 | 16.40 | 24.93 | 5.09 |
| Ag | 2.38 | 1.42 | 1.9 | — |

Alternatively, the third type of optical filter 13 of the present disclosure is shown as an example. In the third type of optical filter 13, based on the total weight of the optical filter 13, the content of titanium is from 18.93 wt % to 20.93 wt %, the content of silver is from 0.26 wt % to 2.26 wt %, the content of barium is from 1.10 wt % to 3.10 wt %, the content of carbon is from 23.28 wt % to 25.28 wt %, the content of oxygen is from 34.09 wt % to 36.09 wt %, and the content of silicon is from 16.33 wt % to 18.33 wt %, and the average of the compositions of the third type of optical filter 13 are shown in Table 3.

TABLE 3

|  | Max | Min | Average |
|---|---|---|---|
| C | 18.33 | 16.33 | 17.33 |
| O | 36.09 | 34.09 | 35.09 |
| Si | 25.28 | 23.28 | 24.28 |
| Ti | 20.93 | 18.93 | 19.93 |
| Ag | 0.26 | 2.26 | 1.26 |
| Ba | 3.10 | 1.10 | 2.10 |

It should be noted that, although the three types of the optical filter 13 are provided here before, all of them are only given to make the disclosure clearer and easier to understand and are not intended to limit the disclosure. In other words, any optical filter that may block input light with an incident angle of greater than 50 degrees may be used as the optical filter 13 of the present disclosure. Hereafter, the principle of blocking input light with an incident angle of greater than 50 degrees by the optical filter is described.

Figure 7:
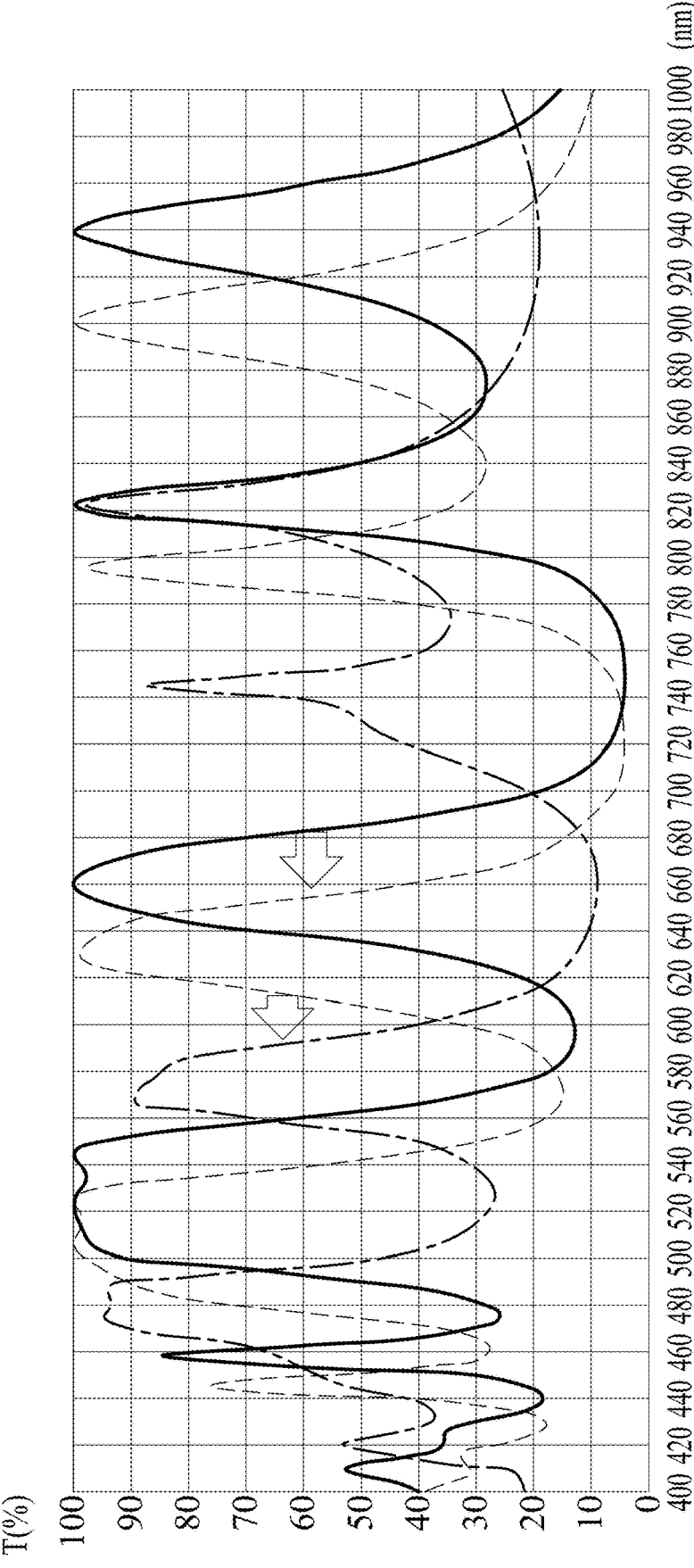
FIG. 7 is a schematic diagram showing the relationship between the spectrum shift and the transmittance according to some embodiments of the present disclosure.

FIG. 7 is a schematic diagram showing the relationship between the spectrum shift and the transmittance. As shown in FIG. 7, when the input light penetrates (passes through)

the optical filter 13 described above by different incident angles, the entire spectral curve of the input light shifts toward the left (i.e., toward short wavelength), which shows the blueshift phenomenon. On the other hand, different wavelengths of the input light correspond to different transmittances. As a result, when the same input light penetrates the optical filter 13 by different incident angles, the amounts of the input light (i.e., the strength of the input light) at a specific wavelength that can be received by the sensing stack 11 are different, which means that the receiving of the input light having an unexpected incident angle by the sensing stack 11 can be reduced. For example, the input light with the incident angle at 0 degrees is shown as the solid line in FIG. 7, the input light with the incident angle at 30 degrees and the input light with the incident angle at 60 degrees are shown as the dotted lines in FIG. 7. The peak of the solid line with the wavelength at 660 nm is shifted to the peaks of the dotted line with the wavelength at 630 nm or 570 nm based on the blueshift phenomenon. Accordingly, at the wavelength of 660 nm, the transmittance of the input light with the incident angle at 0 degrees (about 100%) is greater than the transmittance of the input light with the incident angle at 30 degrees (about 50%) and the transmittance of the input light with the incident angle at 60 degrees (about 10%).

Figure 8:
FIG. 8 is a schematic diagram showing the spectrum according to some embodiments of the present disclosure.
Figure 9:
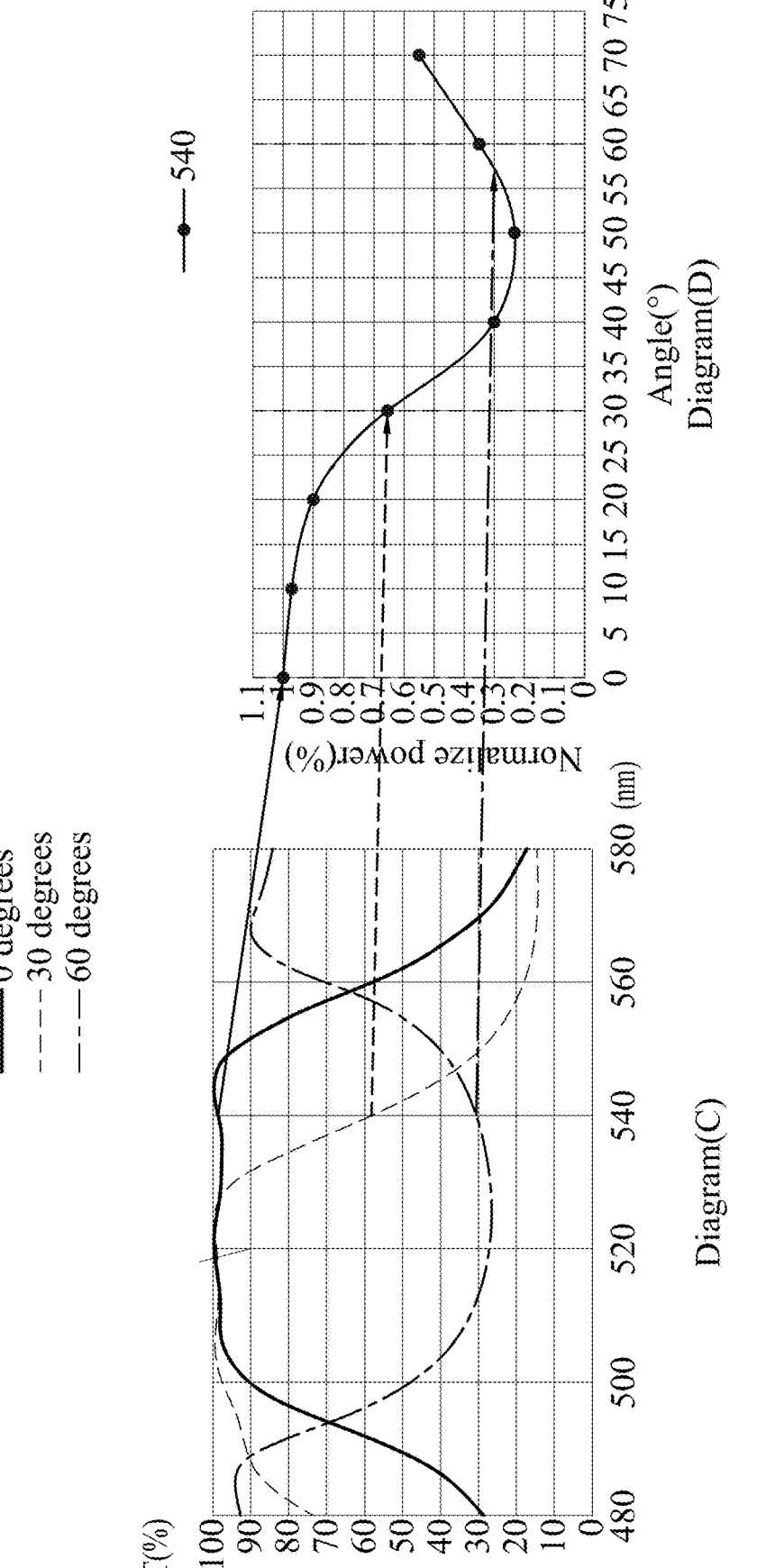
FIG. 9 is another schematic diagram showing the spectrum according to some embodiments of the present disclosure.

Taking the FIG. 8 and FIG. 9 as another example. Among them, diagram (A) of FIG. 8 is a schematic diagram showing the spectrum of the input light at 460 nm to 620 nm before penetrating the optical filter, diagram (B) of FIG. 8 is schematic diagrams showing the transmittances of the input light at 460 nm to 620 nm with different incident angles after penetrating the optical filter, diagram (C) of FIG. 9 is the same as the diagram (B) of FIG. 8, and diagram (D) of FIG. 9 is a schematic diagram showing the transmittances of the input light at 540 nm with different incident angles after penetrating the optical filter. As shown in diagram (A) and diagram (B), when the input light shown in diagram (A) penetrates the optical filter 13, the spectrum of the input light at 520 nm, 540 nm, and 560 nm are shown in diagram (B). Meanwhile, the blueshift of the spectrum of the same input light at 520 nm, 540 nm, and 560 nm that penetrates the optical filter 13 with different incident angles is considered (as shown in diagram (B)). Then, taking the sensing stack using a light with 540 nm for determining the user's physiological characteristics as an example, the spectrum of the input light with different incident angles at 540 nm is shown in diagram (D), wherein the spectrum of diagram (D) is drawn by catching specific nodes (i.e., at 540 nm) of the spectrums of input lights with different incident angles of diagram (C) (i.e. diagram (B)). In diagram (D), the different transmittances of the same input light having different incident angles is shown, and the transmittances of the input light having incident angles of 0 degrees to 30 degrees are greater than the transmittances of the input light having incident angles of 30 degrees to 70 degrees. As mentioned above, the function of blocking the input light having incident angles greater than a specific angle (e.g., 50 degrees) may be achieved.

As shown in FIG. 4, the first electrode 14 is disposed on and electrically connected to the first semiconductor layer 110, and the second electrode 15 is disposed on and electrically connected to the second semiconductor layer 112 and exposed from the optical filter 13. In some embodiments, the first electrode 14 and the second electrode 15 are respectively the cathode electrode and the anode electrode. However, the present is not limited thereto. In some other embodiments, the first electrode 14 and the second electrode 15 may be respectively the anode electrode and the cathode electrode. In some embodiments, there is no coating provided on the first electrode 14 and the second electrode 15. In other words, the first electrode 14 and the second electrode 15 do not directly contact with any coating such as the above-mentioned optical filter 13 or anti-refractive layer 11.

In some embodiments, the first electrode 14 or the second electrode 15 may be include conductive material. The conductive material may include metal, metal compounds, combinations thereof, or other suitable conductive materials, but the disclosure is not limited thereto. For example, the metal may be tin (Sn), copper (Cu), gold (Au), silver (Ag), nickel (Ni), indium (In), platinum (Pt), palladium (Pd), iridium (Ir), titanium (Ti), chromium (Cr), tungsten (W), aluminum (Al), molybdenum (Mo), titanium (Ti), magnesium (Mg), zinc (Zn), germanium (Ge), or their alloys, but the present disclosure is not limited thereto. For example, the metal compound may be tantalum nitride (TaN), titanium nitride (TiN), tungsten silicide ($WSi_2$), indium tin oxide (ITO), antimony zinc oxide (AZO), Tin oxide (SnO), zinc oxide (ZnO), indium zinc oxide (IZO), indium gallium zinc oxide (IGZO), indium tin zinc oxide (ITZO), antimony tin oxide (ATO), etc., but the present disclosure is not limited thereto.

Figure 10:
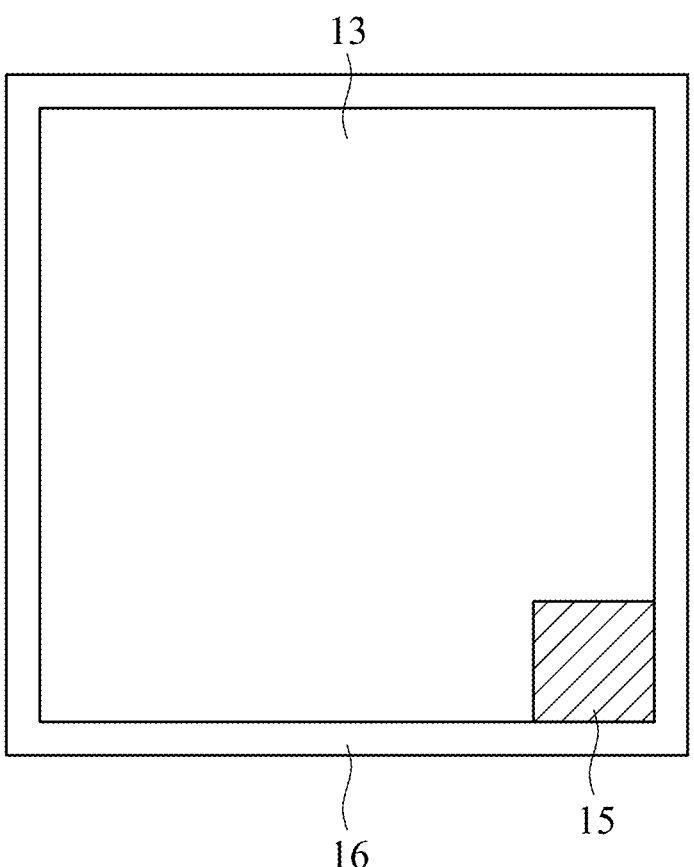
FIG. 10 is a top view showing the photosensitive device according to some embodiments of the present disclosure.

FIG. 10 is a top view showing the photosensitive device according to some embodiments of the present disclosure. As shown in FIG. 4 and FIG. 10, in some embodiments, the photosensitive device 1a further includes the dielectric ring 16 disposed on the intrinsic layer 111 and surrounding the second semiconductor layer 112. In some embodiments, the anti-reflective layer 12 covers the top surface of the dielectric ring 16. More specifically, the dielectric ring 16 may be provided to prevent the second semiconductor layer 112 from unintended electrical connections with other components (not shown) to avoid device failure.

In some embodiments, the material of the dielectric ring 16 may be or may include nitride or oxide, but the present disclosure is not limited thereto. For example, the dielectric ring 16 may be or may include silicon oxide (silicon oxide), silicon nitride (silicon nitride), or silicon oxynitride (SiON).

Figure 11:
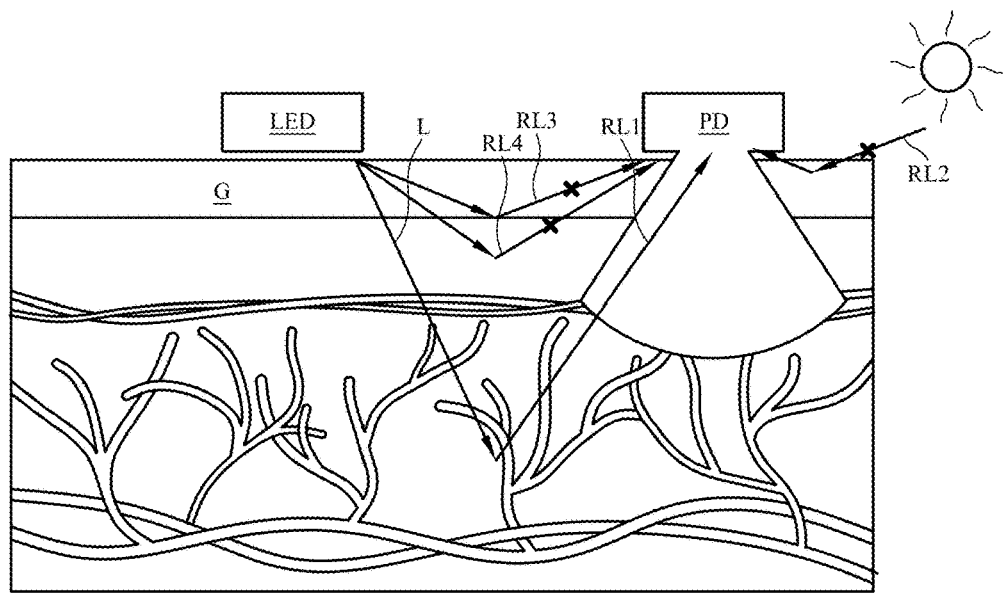
FIG. 11 is a schematic diagram showing the wearable electronic product with the light-emitting device and the photosensitive device according to some embodiments of the present disclosure.

FIG. 11 is a schematic diagram showing the wearable electronic product with the light-emitting device and the photosensitive device according to some embodiments of the present disclosure. As shown in FIG. 11, compared with the wearable electronic product of existing technology (i.e., the photosensitive device provided without an optical filter), the wearable electronic product of the present disclosure may receive the reflected light RL1 from the user's blood at deep skin, while effectively reducing the receiving of reflected light that is unexpected such as the reflected light RL2 of the surrounding environment (e.g., from the sun), the internally reflected light RL3 of the wearable electronic product itself (e.g., from a glass plate of the wearable electronic product), the reflected light RL4 of the user's tissue at superficial skin, and other possible reflected light.

Figure 12:
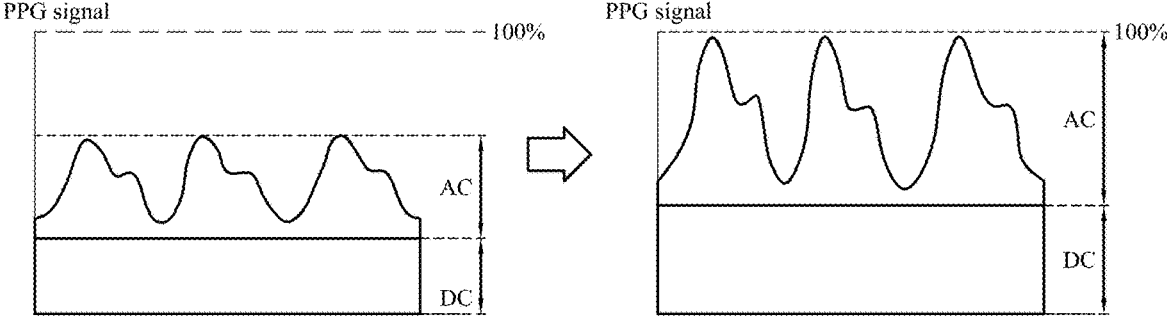
FIG. 12 is a schematic diagram showing the photoplethysmography (PPG) signal according to some embodiments of the present disclosure.

FIG. 12 is a schematic diagram showing the photoplethysmography (PPG) signal according to some embodiments of the present disclosure. As shown in FIG. 12, by the arrangement of the present disclosure, the AC signal may account for a big part (e.g., greater than 60%) of the total measured range of the total range of the photosensitive device, while the DC signal accounts for less than half of the total measured range. As shown in FIG. 12, after enlarging the intensity of the signal (AC+DC) from the photosensitive device provided with an optical filter to be 100% of the intensity of the signal (AC+DC) from the photosensitive device provided without an optical filter, the AC signal will be very significant, which helps in the identification of physiological characteristics.

Figure 13:
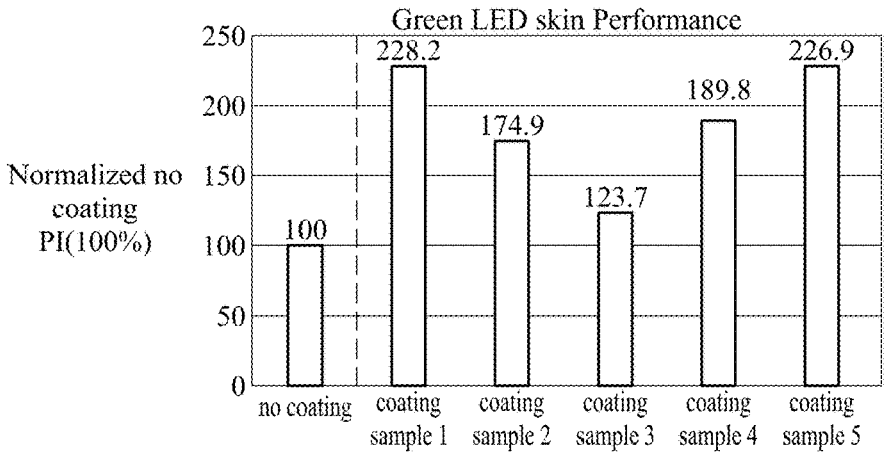
FIG. 13 is a schematic diagram showing the perfusion index (PI) of the green-light LED according to some embodiments of the present disclosure.
Figure 14:
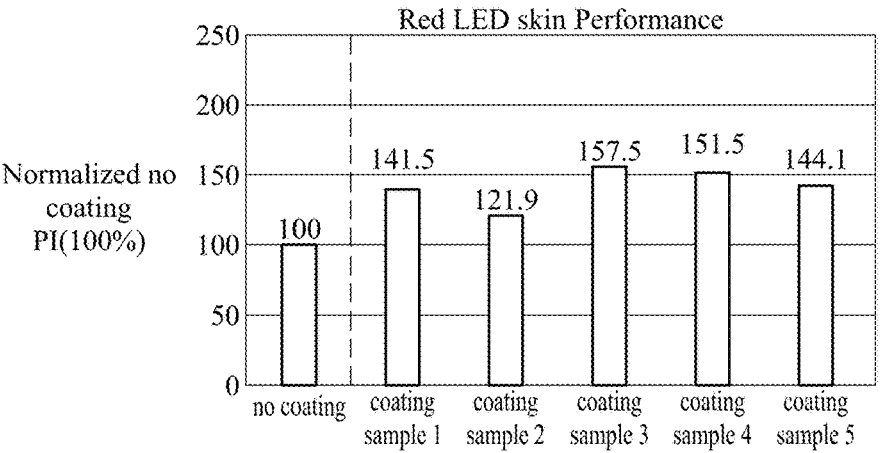
FIG. 14 is a schematic diagram showing the perfusion index (PI) of the red-light LED according to some embodiments of the present disclosure.
Figure 15:
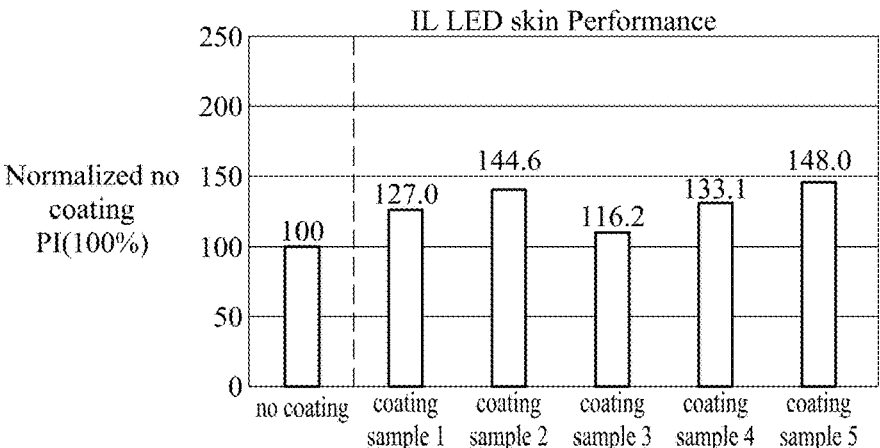
FIG. 15 is a schematic diagram showing the perfusion index (PI) of the IL-light LED according to some embodiments of the present disclosure.

FIGS. 13-15 are schematic diagrams showing the normalized perfusion indexes (PI) of the green-light LED, red-light LED, and IL-light LED. In the present disclosure, the normalized perfusion indexes (PI) indicates the PI ratio that equals the PI value of the photosensitive device provided with an optical filter divided by the PI value of the photosensitive device provided without an optical filter. As shown in FIGS. 13-15, no matter which light source the wearable device uses (for example, green light, red light, or infrared light), PI may be significantly improved. For example, the PI ratio of the green light of the photosensitive device provided with an optical filter is at least 123.7%. Similarly, the PI ratio of the red light of the photosensitive device provided with an optical filter is at least 121.9%. Similarly, the PI ratio of the IL light of the photosensitive device provided with an optical filter is at least 116.2%. In this way, the significant improvement of PI significantly improves the identification of physiological characteristics.

Figure 16:
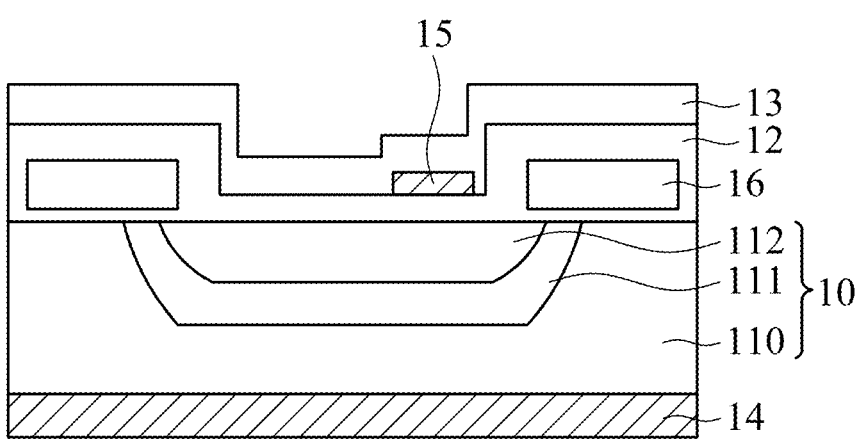
FIG. 16 is a schematic diagram showing the photosensitive device according to some other embodiments of the present disclosure.

FIG. 16 is a schematic diagram showing the photosensitive device according to some other embodiments of the present disclosure. As shown in FIG. 16, the photosensitive device 1a' includes the substrate 10, the anti-reflective layer 12, the optical filter 13, the first electrode 14, and the second electrode 15. More specifically, the difference between the photosensitive device shown in FIG. 16 and the photosensitive device shown in FIG. 4 is that the intrinsic semiconductor layer 111 is surrounded by the first semiconductor layer 110 in FIG. 16.

Figure 17:
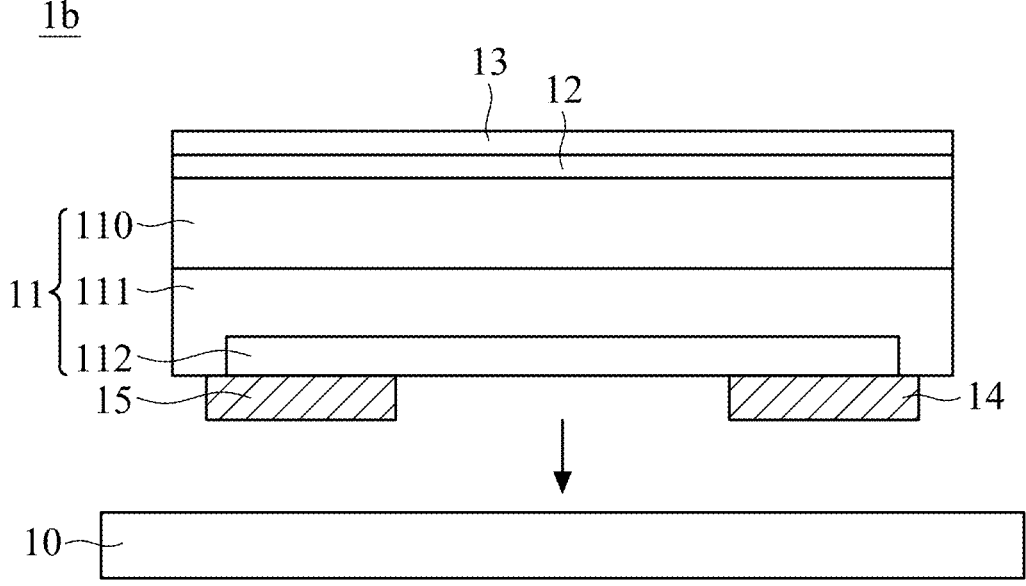
FIG. 17 is a schematic diagram showing the photosensitive device according to some other embodiments of the present disclosure.
Figure 18:
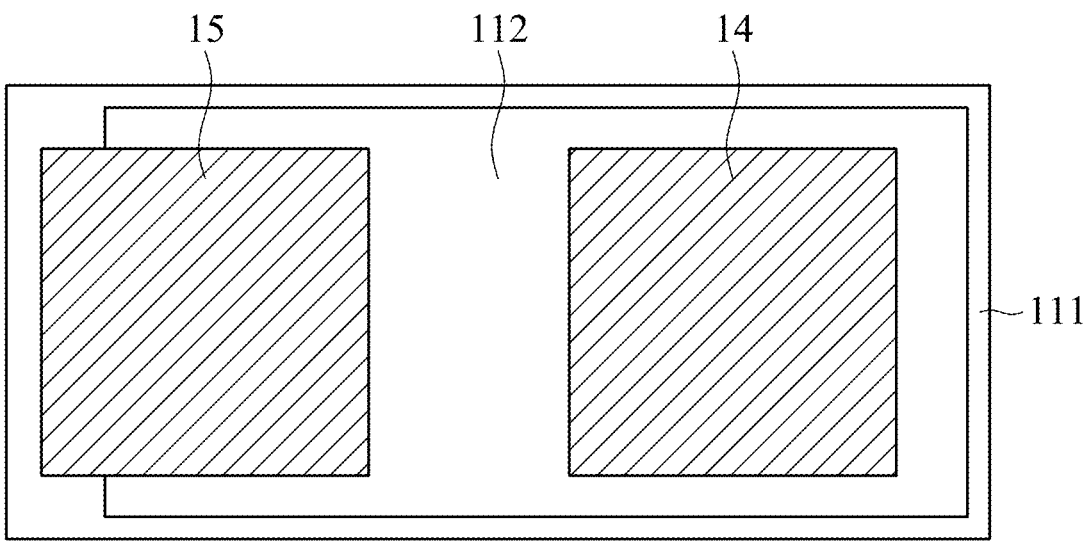
FIG. 18 is a bottom view showing the photosensitive device according to some embodiments of the present disclosure.

FIG. 17 is a schematic diagram showing the photosensitive device according to some other embodiments of the present disclosure, and FIG. 18 is a bottom view showing the photosensitive device according to some embodiments of the present disclosure. As shown in FIGS. 17-18, the photosensitive device 1b includes the substrate 10, the anti-reflective layer 12, the optical filter 13, the first electrode 14, and the second electrode 15. More specifically, in these embodiments, the first electrode 14 and the second electrode 15 are both on the same side of the first semiconductor layer 110 opposite the intrinsic layer 111.

In these embodiments of FIGS. 17-18, the arrangement of the photosensitive device 1b is called a flip-type structure. In other words, the optical filter 13 of the present disclosure may be not only used in the vertical-type structure of the photosensitive device but also in the flip-type structure of the photosensitive device.

Figure 19:
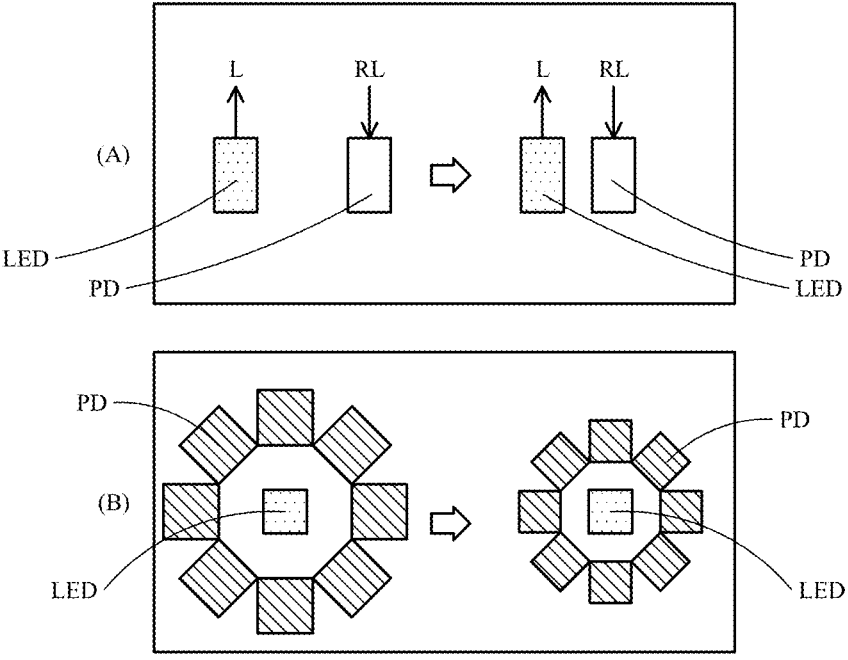
FIG. 19 is schematic diagram showing the photosensitive device according to some embodiments of the present disclosure.

As mentioned above, the measured signal feedback may be improved by the photosensitive device provided with an optical film, so the distance between the light-emitting element and the light-receiving element (i.e., the sensing stack) may be shortened to reduce the overall module design. FIG. 19 is schematic diagrams showing the photosensitive device according to some embodiments of the present disclosure.

As shown in FIG. 19, due to the DC signal decrease significantly and the AC signal decrease slightly, the noise decreases significantly. Therefore, the distance between the light-emitting element (LED) and the light-receiving element (PD) may be shortened as but not limited to the way shown in (A) and (B) of FIG. 19.

Figure 20:
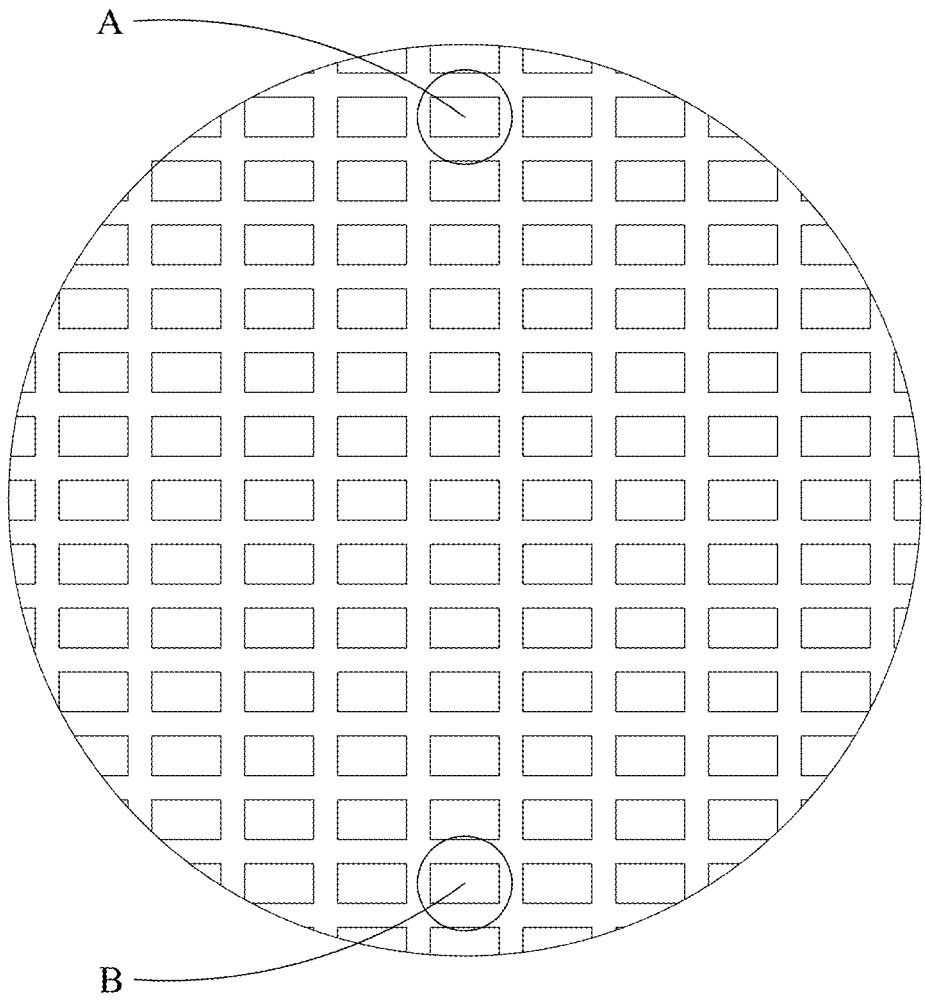
FIG. 20 is a schematic diagram showing the wafer coated with an optical film according to some embodiments of the present disclosure.

FIG. 20 is a schematic diagram showing the wafer coated with an optical film according to some embodiments of the present disclosure. As shown in FIG. 20 and Table 4, the measurement of the light-receiving angle of the sensing element, the light-receiving angle is significantly converged when the collimation structure is provided. For example, in area A of the wafer and area B of the wafer, the light-receiving angle of the photosensitive device with a collimation structure (i.e., optical film) is significantly lower than the light-receiving angle of the photosensitive device without a collimation structure (i.e., optical film).

TABLE 4

| Wafer | Position | Item | Angel No. | measurement of light-receiving angle (half angle) | | |
| | | | | Green-light | Red-light | IR-light |
|---|---|---|---|---|---|---|
| without collimation structure (i.e., optical film) | | without glue | No. 1 | 58.5 | 61.5 | 58.5 |
| | | | No. 2 | 57 | 58.5 | 60 |
| | | with glue | No. 1 | 60 | 61.5 | 61.5 |
| | | | No. 2 | 60 | 60 | 61.5 |
| with collimation structure (i.e., optical film) | upper area A of wafer | without glue | No. 1 | 40.5 | 25.5 | 33 |
| | | | No. 2 | 40.5 | 25.5 | 34.5 |
| | | with glue | No. 1 | 42 | 27 | 37.5 |
| | | | No. 2 | 40.5 | 25.5 | 38 |
| | lower area B of wafer | without glue | No. 1 | 37.5 | 22.5 | 33 |
| | | | No. 2 | 37.5 | 25.5 | 31.5 |
| | | with glue | No. 1 | 37.5 | 24 | 31.5 |
| | | | No. 2 | 39 | 24 | 36 |

In summary, the present disclosure provides a photosensitive device that can block input light having an incident angle greater than 50 degrees, so as to effectively measure the user's physiological characteristics. In addition, due to the measured signal feedback being enough, the distance between the light-emitting element and the light-receiving element (i.e., the sensing stack) may be shortened to reduce the overall module design. Moreover, the angle of light blocked by the optical filter may be changed to target reflected light from different skin depths.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A photosensitive device, comprising:
  a sensing stack comprising:
    a first semiconductor layer;
    an intrinsic semiconductor layer disposed on the first semiconductor layer; and
    a second semiconductor layer disposed on the intrinsic semiconductor layer;
  an optical filter disposed on a side of the sensing stack and comprising high refractive films and low refractive films alternately stacked, wherein the optical filter blocks any input light having an incident angle greater than 50 degrees;

an anti-reflective layer disposed between the sensing stack and the optical filter; and
  a first electrode and a second electrode connected to the sensing stack;
  wherein the total number of the high refractive films and the low refractive films is thirteen or more than thirteen.

2. The photosensitive device as claimed in claim 1, wherein a refractive index of the high refractive films and low refractive films is from 1.3 to 2.5.

3. The photosensitive device as claimed in claim 2, wherein the refractive index of the high refractive films is from 2.0 to 2.5 and the refractive index of the low refractive films is from 1.3 to 1.5.

4. The photosensitive device as claimed in claim 1, wherein a thickness of the optical filter is from 1500 nm to 1950 nm.

5. The photosensitive device as claimed in claim 1, wherein the optical filter comprises a metal element.

6. The photosensitive device as claimed in claim 5, wherein the metal element comprises sodium, niobium, titanium, silver, barium, or a combination thereof.

7. The photosensitive device as claimed in claim 1, wherein a material of the anti-reflective layer comprises silicon nitride.

8. The photosensitive device as claimed in claim 1, wherein a thickness of the anti-reflective layer is from 50 nm to 100 nm.

9. The photosensitive device as claimed in claim 1, wherein the first electrode and the second electrode are both on the same side of the first semiconductor layer opposite the intrinsic semiconductor layer.

10. The photosensitive device as claimed in claim 1, wherein the first electrode is disposed on the first semiconductor layer, and the second electrode is disposed under the second semiconductor layer.

11. The photosensitive device as claimed in claim 10, further comprising a dielectric ring disposed on the intrinsic semiconductor layer and surrounding the second semiconductor layer.

12. The photosensitive device as claimed in claim 10, wherein the dielectric ring is in direct contact with the intrinsic semiconductor layer.

13. The photosensitive device as claimed in claim 12, wherein the intrinsic semiconductor layer is surrounded by the first semiconductor layer.

14. The photosensitive device as claimed in claim 10, wherein the anti-reflective layer covers a top surface of the dielectric ring.

15. The photosensitive device as claimed in claim 1, wherein the anti-reflective layer is a continuous layer.

16. The photosensitive device as claimed in claim 1, wherein the optical filter is a continuous layer.

17. The photosensitive device as claimed in claim 1, wherein the optical filter comprises silicon.

18. The photosensitive device as claimed in claim 1, wherein the first electrode comprises a side surface covered by the anti-reflective layer.

19. The photosensitive device as claimed in claim 1, wherein the anti-reflective layer directly contacts the sensing stack.

\* \* \* \* \*